United States Patent [19]

Bastioli et al.

[11] Patent Number: 4,725,631
[45] Date of Patent: Feb. 16, 1988

[54] ACRYLIC DIESTERS OF BISPHENOL-ALKYL-ETHER, POLYMERS PREPARED THEREFROM, AND COMPOSITES FOR DENTAL USE

[75] Inventors: Catia Bastioli, Novara; Giancarlo Romano, Turin; Romano Mazzocchi, Pernate, all of Italy

[73] Assignee: Montedison S.p.A., Milan, Italy

[21] Appl. No.: 887,815

[22] Filed: Jul. 21, 1986

[30] Foreign Application Priority Data

Jul. 26, 1985 [IT] Italy ............................... 21732 A/85

[51] Int. Cl.$^4$ ........................ A61K 6/00; A61F 2/00
[52] U.S. Cl. ................................. 523/115; 523/116; 523/120; 525/531; 526/292.3; 526/246; 560/221; 560/223
[58] Field of Search ............... 525/531; 523/109, 120, 523/115, 116; 106/35; 560/221, 223; 526/292.3, 246

[56] References Cited

U.S. PATENT DOCUMENTS

| | | | |
|---|---|---|---|
| 4,091,225 | 5/1978 | Parker | 560/221 |
| 4,439,291 | 3/1984 | Irving et al. | 525/502 |
| 4,468,524 | 8/1984 | Zahir et al. | 560/221 |
| 4,616,073 | 10/1986 | Antonucci | 526/246 |
| 4,633,023 | 12/1986 | Griffith | 560/221 |

Primary Examiner—Theodore Morris
Attorney, Agent, or Firm—Stevens, Davis, Miller & Mosher

[57] ABSTRACT

Acrylic diesters of bisphenol-alkyl-ether of formula:

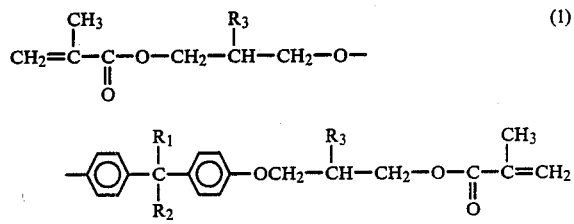

in which $R_1$ and $R_2$ may be a halogen or a $C_1$–$C_7$ alkyl radical optionally halogen-substituted, and $R_3$ may be hydrogen, halogen, or a $C_1$–$C_7$ alkyl radical optionally halogen-substituted. Polymers obtained from the acrylic diesters of bisphenol-alkyl-ether of formula (1) and dental composites containing said acrylic diesters.

17 Claims, No Drawings

ACRYLIC DIESTERS OF BISPHENOL-ALKYL-ETHER, POLYMERS PREPARED THEREFROM, AND COMPOSITES FOR DENTAL USE

This invention relates to alkylic diesters of bisphenol-alkyl-ether, to the polymers prepared therefrom, and to composites for dental prosthesis containing said diesters.

As is known, for the preparation of dental fillers, crowns, bridges and parts to be substituted, there have been utilized in addition to gold and porcelain, also synthetic substances such as the polymers prepared from unsaturated compounds of the olefinic type which are easily polymerizable. These polymeric substances offer substantial advantages with respect to dental prostheses made of gold or of porcelain, as regards appearance. These polymeric substances actually permit one to better imitate the color of natural teeth.

In recent years, the polymeric substances which are being used most broadly in dentistry for the manufacture of dental fillings, crowns, artificial teeth, and repairing work in general are polymethacrylates. Said polymethacrylates are generally obtained by thermal, chemical or photochemical polymerization of methyl-methacrylate, so as to obtain a satisfactory degree of polymerization.

More recently, other synthetic substances, such as for example polyamides, polycarbonates and, chiefly, a great number of esters of methacrylic acid, have been synthesized and tested for their utilization in the field of dentistry.

However, endeavors made to substitute methyl-methacrylate with other derivatives of acrylic or methacrylic acid were not successful enough, so that methyl-methacrylate has remained the most used compound in the field of dentistry.

As is well known, for dental restorations polymerization can be conducted only at room temperature or at human body temperature. The main drawback of this cold polymerization consists in that a minor part of methyl-methacrylate remains non-polymerized and can gradually be released outside the composition. For this reason, the fillers based on methyl-methacrylate are utilized only in case of devitalized teeth.

With a view to improving the mechanical properties and, in particular, the resistance to abrasion of the synthetic substances, a few difunctional esters of methacrylic acid have been prepared which give rise to tri-dimensionally crosslinked products. The use of a few of these difunctional esters in the manufacture of dental prosthesis or fillings is described in U.S. Pat. No. 3,066,112 (Bowen).

The difunctional ester of methacrylic acid described in the Bowen patent is prepared through the reaction of phenols, in particular bis-phenol A, with glycidyl methacrylate, giving rise to the following compound:

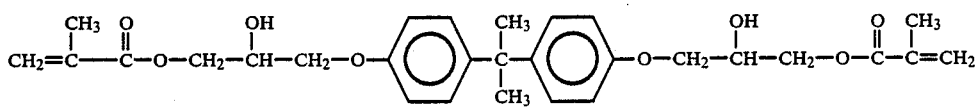

generally known as Bowen resin or resin BIS-GMA. The polymerization of such diester is started by an activator and by a catalyst, generally benzoyl peroxide, in the presence of diluents and of organic fillers.

The resin BIS-GMA, however, exhibits in practice various drawbacks which limit the use thereof. It exhibits, for example, a very high viscosity, of the order of 100 poises, with the consequent necessity of adding low molecular weight substances both to obtain high concentrations of filler in the composite and to achieve an acceptable degree of conversion.

In order to lower the viscosity of these resins there are added reactive diluents of the type of methyl-methacrylate, of dimethacrylate glycols, such as for example ethyleneglycol-dimethacrylate, and preferably triethyleneglycol-dimethacrylate, or other suitable reactive extenders having a low molecular weight. The presence of these low molecular weight monomers entails various drawbacks such as a high shrinkage during polymerization, the release of unreacted low molecular weight substances which are toxic for the dental pulp, plastification defects of the matrix, and the like.

The BIS-GMA resins, furthermore, are not fully inert to moisture and, in the presence of water or saliva, suffer from a decay of their mechanical properties, color changes due to degradation processes, microcavitation and plastification defects, with consequent release of unreacted monomers.

It has now, surprisingly, been found, and this is the object of the present invention, that composites for dental use, such as parts to be replaced, synthetic teeth, inner parts of a tooth, covering crowns, prosthesis articles, and other dental preparations endowed with higher resistance and stability properties as well as a low absorption of water, are obtainable when the monomer to be polymerized is a difunctional compound of an acrylic diester of bisphenol alkyl-ether of formula:

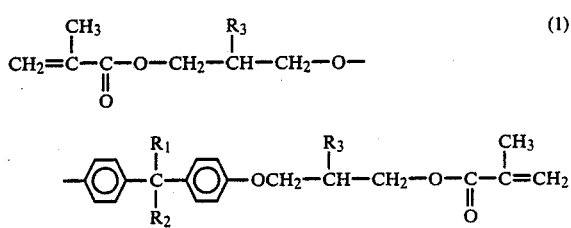

in which $R_1$ and $R_2$ may be, independently of each other, a halogen atom, a linear or branched alkyl radical containing from 1 to 7 carbon atoms with, optionally, one or more hydrogen atoms substituted by a halogen such as fluorine, chlorine or bromine; and $R_3$ may be a hydrogen atom, a halogen atom, a linear or branched alkyl radical containing from 1 to 7 carbon atoms with, optionally, one or more hydrogen atoms substituted by halogen such as fluorine, chlorine or bromine; provided that, when $R_3$ is hydrogen, $R_1$ and $R_2$ are alkyl radicals containing halogen.

According to a preferred embodiment of the present invention, $R_1$ and $R_2$ are halo-alkyl radicals, in particular per-fluoro-alkyl radicals and preferably $-CF_3$, and $R_3$ is an alkyl radical, in particular a methyl radical.

One or more hydrogen atoms of the two benzene rings of the acrylic diester of formula (1) may be substituted by alkyl or alkoxy radicals having a low number of carbon atoms, i.e. ranging from 1 to 4.

The acrylic diesters of bisphenol-alkyl-ether of formula (1) are generally low-viscosity liquids or relatively low-melting solid substances. They are preparable by per se conventional methods of esterification or trans-esterification. For example, the diols of p,p'-di-hydroxy-di-phenyl-alkane or of halogenated p,p'-di-hydroxy-di-phenyl-alkane may be directly esterified with acrylic or methacrylic acid in the presence of known esterification catalysts such as, for example, p.toluene-sulphonic acid. The preparation of the difunctional monomers of formula (1) may be also conducted by trans-esterification of alkyl-esters of the acrylic or methacrylic acid, for example of methyl ester, with the diols mentioned hereinbefore, in the presence of an acid or a basic catlyst. Particularly advantageous is the preparation of the difunctional monomers of formula (1) by reaction of the diols with reactive derivatives of the acrylic or methacrylic acid, such as for example the chloride or the anhydride.

The addition of a dehydrating agent may also prove to be advantageous. It is preferable to operate in an inert gas atmosphere, as well as to employ a per se conventional polymerization inhibitor, such as for example 2,6-di-substituted phenol.

The diols of p,p'-di-hydroxy-di-phenyl-alkane or of halogenated p,p'-di-hydroxy-di-phenyl-alkane are preparable by alkylation, with methallyl chloride, or bisphenol as such or of halogenated bisphenol, in particular fluorinated bisphenol, and by subsequent hydroboration and oxidation of the obtained vinyl-ether, according to the following reaction scheme:

The impure diol (V) initially obtained may be purified by chromatography on a silica gel column.

The polymerization of the acrylic diester of bisphenol-alkyl-ether (I) is conducted in a per se conventional manner in the presence of substances capable of forming free radicals such as peroxides, nitriles of azo-carboxylic acid, redox catalysts, etc. Utilizable peroxides are e.g. benzoyl peroxide, lauryl peroxide, mono-ter.butyl-permaleate or ter.butyl-hydroperoxide. For the manufacture of substitution moieties which are prepared separately, polymerization is carried out with lauryl peroxide by heating the mass placed in a mold, at a temperature ranging from 90° to 160° C. during a short period of time. It is preferable to conduct the polymerization at 120°–160° C. in a hot air stream in order to achieve the highest possible degree of cross-linking.

For the preparation of dental cements directly in the mouth, there are utilized substances which are capable of acting as starters at room temperature or at the temperature of the human body, in particular redox systems. It is preferable to use substances which do not tend to change color or to become dark. Suitable redox catalysts are benzoyl peroxide with N,N'-dimethyl-para-toluidine, hydroperoxides with thioureas, ethyl hydroperoxide with N,N-dimethyl-paratoluidine, benzoyl ethers such as methyl-benzyl-ether with an ammonium activator, alpha-diketones and methyl-amines, etc. The catalysts are employed in a catalytic amount generally ranging from 0.05 to 5% by weight based on the monomer.

Although an advantage of the dental composite and of the other dentistry products prepared according to the present invention resides in the possibility of not adding any diluents, in a few particular cases such addition may be advantageous.

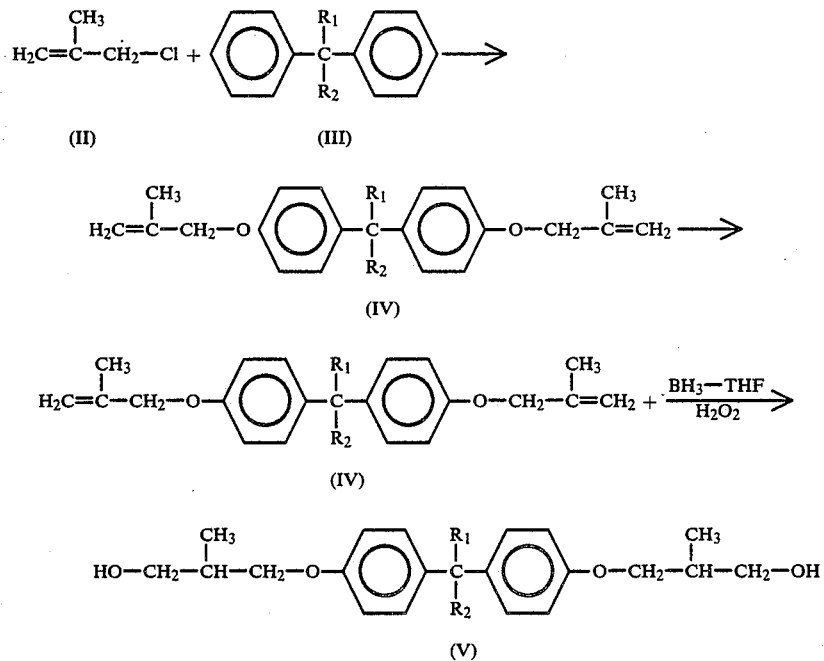

The BH$_3$—THF (tetrahydrofuran) complex is prepared from NaBH$_4$ and BF$_3$—(C$_2$H$_5$)$_2$O in diglyme.

Oxidation is accomplished with H$_2$O$_2$ in the presence of HaOH.

Suitable diluents are generally the esters of acrylic or methacrylic acid having a low molecular weight, such as for example ethylene glycol-dimethacrylate; tri-ethyleneglycol-dimethacrylate; tetra-ethyleneglycoldimethacrylate; bispehnol-dimethacrylate; methylmethacrylate; and fluorinated diluents such as perfluoroalkyl methacrylates, alkylmethacrylates or alkyl-dimethacrylates.

Polymerization is generally conducted in the presence of fillers. Particularly advantageous fillers are quartzes, silicas, Al-, Ba- Sr-silicates and the like, zirconates, aluminas, preferably those having a low surface area, with particle diameters below 40 μm, and treated with silanes of the type of methacryl-oxypropyl-silane, galss fibers, carbon fibers, etc., submicronic inorganic fillers, brought to sizes of the order of 10-40 micrometers by means of coating with methacrylate resins.

The amount of such fillers in the compositions may bary over a wide range, although concentrations in the range of from 30 to 86%, and preferably from 50 to 80% by weight, referred to the total weight of the composition, are generally used.

Another advantage of the present invention is that the diesters of formula (I) provide high degrees of conversion of the double methacrylic bonds in the polymerized, do not represent a danger for the dental pulp. In fact, said monomers possess little mobility inside the matrix, which is polymerized, due to their high molecular weight.

Another advantage of the dental filler or of the part prepared from the polymer of the present invention is that the composites thereof do not undergo dimensional variations even if in contact with water and saliva during long periods of time.

A further advantage of the resins prepared by polymerization of the acrylic diesters of formula (I), and in particular of the composites which utilize such resins as a matrix, is represented by their very low water absorption. Since, as is known, the absorption of water involves dimensional changes and a faster worsening of the mechanical and chemical-physical properties of the manufactured article, the products of the present invention possess a chemical inertness much higher than that of the corresponding commercial products.

The following examples are given to still better illustrate the present invention, without being however a limitation thereon.

EXAMPLE 1

Into a 10-liter reactor there were introduced 626 g of methallyl chloride, 1000 g of fluorinated bisphenol A dissolved in 61 g of dimethyl formamide, and 392 g of potassium hydroxide at 85%.

This reaction mixture was maintained at 30° C. for 8-10 hours. The methallyl ester of fluorinated bisphenol A thus obtained was separated, washed with hexane and water, and dried over $Na_2SO_4$.

There were obtained 1298 g of

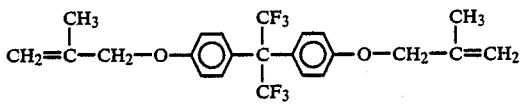

with a yield of 90-95%.

The product so obtained was trasformed into the corresponding diol through a hydroboration-oxidation reaction. For this purpose, 2332 g of $BF_3(C_2H_5)_2O$ were gradually added under stirring to 500 g of $NaBH_4$ dissolved in 3.4 l of diglyme, maintained at 0° C., in a gastight reactor. The temperature was brought to 60° C. and maintained at such value during 24 hours. The liberated $BH_3$ was absorbed in tetrahydrofuran.

In a gas-tight reactor, the fluorinated dimethallyl-bisphenol A prepared as described hereinbefore was added dropwise to the $BH_3$-tetrahydrofuran solution. The reaction mass was kept at 50° C. during 24 hours under continuous stirring.

The organo-borane so obtained was diluted with 1500 ml of water and oxidized with 660 ml of hydrogen peroxide at 35% by volume. The resulting diol was purified on a silica gel column.

1100 g of pure diol were reacted with 593 g of methacryloyl-chloride, in the presence of 872 ml of triethylamine, in 10 l of $CH_2Cl_2$. The esterification reaction was accomplished at −2° C. during 1 hour.

The final product was washed with solutions of HCl at 5% and NaOH at 40%, and then it was dried.

964 g of methacrylic diester were obtained, the yield being 68% referred to the diol.

EXAMPLE 2

The monomer of Example 1 was polymerized in the presence of 2% of benzoyl peroxide at 80° C. for 30 minutes and separately for 5 hours at 110° C. Samples were prepared measuring 4 cm×1 cm×0.5 mm, which were immersed in water at 37° C., 48° C., and 60° C.

Each sample exhibited an absorption of water of about 0.45% by weight.

The samples were subjected to I.R. analysis in order to determine the degree of conversion of the methacrylic double bonds. The test was conducted by grinding 100 mg of the sample in liquid nitrogen and by dispersing the resulting powder in KBr.

The absorbance variation of the band at 1639 $cm^{-1}$ relating to the double bonds in comparison with the band at 1580 $cm^{-1}$ of the aromatic ring, in the conversion from monomer to polymer, permits one to determine the number of reacted double bonds. The samples exhibited conversion degrees of 95-96%.

EXAMPLE 3

By using silanized quartz, whose particles had average sizes around 10 μm and a surface area of 1.5 $m^2/g$, there were prepared two pastes consisting of:

(A)

3 g of methacrylic diester of Example 1,
7 g of silanized quartz, and
0.06 g of benzoyl peroxide, (B)

3 g of methacrylic diester of Example 1,
7 g of silanized quartz, and
0.03 g of dimethyl-para-toluidine.

By mixing 50% by weight of paste A with 50% by weight of paste B, there were prepared a few samples having dimensions: 4 cm×1 cm×0.5 mm.

The samples so obtained, after polymerization at 80° C. for 3 minutes, exhibited a water absorption at 37° C., 48° C., and 60° C. of about 0.15% by weight.

EXAMPLE 4

By substituting the quartz filler of Example 3 with alumina having a surface area of 4 $m^2/g$, an average particle size of 0.5 μm, and a narrow particle size distribution, samples were obtained having a water absorption of about 0.12%.

The static flexural tests carried out on such samples gave the following results:

Elastic modulus: 135,000 kg/cm$^2$

Tensile strength: 980 kg/cm$^2$.

What is claimed is:

1. Acrylic diester of bisphenol-alkyl-ether having the formula:

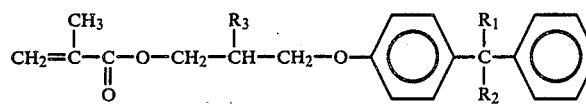

in which $R_1$ and $R_2$ are halo-alkyl radicals; and $R_3$ may be a hydrogen atom, a halogen atom, a linear or branched alkyl radical containing from 1 to 7 carbon atoms with one or more hydrogen atoms substituted by halogens such as fluorine, chlorine or bromine.

2. Acrylic diester of bisphenol-alkyl-ether according to claim 1, in which $R_1$ and $R_2$ are perfluoroalkyl radicals.

3. Acrylic diester of bisphenol-alkyl-ether according to claim 2, in which $R_1$ and $R_2$ are —$CF_3$.

4. Acrylic diester of bisphenol-alkyl-ether according to claim 1 or 2 or 3, in which $R_3$ is an alkyl radical.

5. Acrylic diester of bisphenol-alkyl-ether according to claim 4, in which $R_3$ is a methyl radical.

6. Acrylic diester of bisphenol-alkyl-ether according to any one of claims 1 or 2 or 3, in which one or more hydrogen atoms of the two benzene rings is/are substituted by alkyl radicals or alkoxy radicals containing 1 to 4 carbon atoms.

7. Acrylic resins containing repeating units of acrylic diester of bisphenol-alkyl-ether of formula:

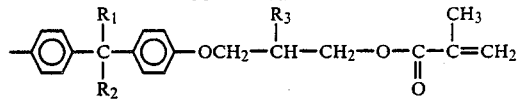

in which $R_1$ and $R_2$ are halo-alkyl radicals; and $R_3$ may be a hydrogen atom, a halogen atom, a linear or branched alkyl radical containing from 1 to 7 carbon atoms with one or more hydrogen atoms substituted by halogens such as fluorine, chlorine or bromine.

8. Acrylic resins according to claim 7, in which $R_1$ and $R_2$ are perfluoro-alkyl radicals.

9. Acrylic resins according to claim 8, in which $R_1$ and $R_2$ are —$CF_3$.

10. Acrylic resins according to claim 7 or 8 or 9, in which $R_3$ is a methyl radical.

11. Acrylic resins according to claim 7 or 8 or 9, in which one or more hydrogen atoms of the two benzene rings is/are substituted by alkyl or alkoxy radicals containing 1 to 4 carbon atoms.

12. Dental composites comprising an acrylic diester of bisphenol-alkyl-ether having formula (I), as defined in claim 1, at least one inorganic filler, and a catalytic amount of a redox catalyst system.

13. Dental composites according to claim 12, in which the amount of inorganic filler ranges from 30 to 85% by weight.

14. Dental composites according to claim 13, in which the amount of inorganic filler ranges from 50 to 80% by weight.

15. Dental composites according to claim 12 or 13 or 14 in which the inorganic fillers are selected from the class consisting of quartzes, silicas, silicates of Al, Ba, and Sr, zirconates, aluminas having a low surface area, particle diameters below 40 μm, and are treated with silanes, glass fibers or carbon fibers, and submicronic inorganic fillers, brought to sizes of the order of 10–40 μm and coated with methacrylcates.

16. Dental composites according to claim 12 or 13 or 14, in which the amount of the redox catalyst system ranges from 0.05 to 5% by weight referred to the monomer.

17. Dental composites according to claim 12 or 13 or 14, containing a diluent.

* * * * *